United States Patent [19]

Kamimae et al.

[11] 4,338,304

[45] Jul. 6, 1982

[54] COMPOSITE FOR TREATING DIABETES

[75] Inventors: Hiroshi Kamimae, Yokohama; Tadashi Ishikawa, Sagamihara, both of Japan

[73] Assignee: Nihon Nosan Kogyo Kabushiki Kaisha, Yokohama, Japan

[21] Appl. No.: 195,638

[22] Filed: Oct. 9, 1980

[30] Foreign Application Priority Data

Oct. 29, 1979 [JP] Japan .............................. 54/138764

[51] Int. Cl.³ .............................................. A61K 33/18
[52] U.S. Cl. ................................................. 424/150
[58] Field of Search ........................................ 424/150

[56] References Cited

U.S. PATENT DOCUMENTS 4,187,294  2/1980  Ishikawa et al. .................... 424/150

Primary Examiner—Frederick E. Waddell
Attorney, Agent, or Firm—Martin Smolowitz

[57] ABSTRACT

A composite used for treating diabetes. The effective component of the composite is an egg containing much iodine. The egg is obtained by feeding to egg-laying birds a feed into which an iodine compound and/or a seaweed are mixed.

1 Claim, No Drawings

COMPOSITE FOR TREATING DIABETES

TECHNICAL FIELD

The present invention relates to a composite for treating diabetes of which the effective component is an egg containing a high amount of iodine.

In the prior art, internal medicines for treating diabetes are synthetic blood sugar lowering agents, which includes sulphonyl urea agents such as tolbutamide and biguanide agents such as phenformin. However, as the synthetic medicines meet problems in a practical effect and in adverse reactions, it is still expected to develop effective medicines for treating diabetes which are easily applicable and have no adverse reactions. On the other hand, a dietetic treatment is very important to cure diabetes, and it is generally said that medicines are supplementary means for the dietetic treatment.

DISCLOSURE OF INVENTION

We, inventors, have made a variety of researches on the basis of such situation and viewpoint, and obtained the knowledge that it would be very effective in treating diabetes to administrate eggs containing much iodine for a given period. And, we completed the present invention in accordance with the knowledge.

Namely, an object of the present invention is to provide a composition for treating diabetes which is stable and effective in promoting insulin secretion without any adverse actions. And, the feature of the present invention is that eggs containing much iodine are used as an effective component of the composition or composite.

According to our investigations, there is no report that iodine or composites containing iodine are effective in treating diabetes, so that the present invention may be called as a pioneer invention.

MODE OF CARRYING OUT THE INVENTION

Eggs containing a high amount of iodine used in the present invention are usually obtained as follows;

Namely, an iodine compound and/or a seaweed containing much iodine are mixed into a feed in excess of a fixed quantity, and then the feed is given or dosed to egg-laying birds in order to increase the iodine content of egg. The iodine compound includes calcium iodate, potassium iodate, sodium iodate, potassium iodide, sodium iodide, cuprous iodide, thymol iodide, calcium iodobehemate, diiode salicylic acid, calcium periodate. The seaweed includes a wakame, a kombu and the like.

In the case of the present invention, calcium iodate is the most desirable iodine compound, and it is further preferable to use calcium iodate together with the seaweed such as kombu. The dosage amount of iodine is varied dependently on the kind of egg-laying birds such as a hen, a quail and so on. In the case of hens, assuming that one head of hen ingests a feed of about 100 g per day, the iodine is mixed so that the iodine content of the feed may be 50 to 2,500 ppm.

Thus, as a result of dosing the iodine compound or seaweed to egg-laying birds, eggs containing much iodine are produced after about a week. For example, in the case of egg-laying hens, where the feed containing iodine of about 50 ppm is fed, eggs containing iodine of about 300 μg per egg are produced. And where the feed containing iodine of about 100 ppm is used, eggs containing iodine of about 600 to 800 μg per egg are produced.

The eggs containing much iodine may be used as the composite for treating diabetes under the non-processed state. They also may be used after a suitable process, for example, drying, concentrating, powdering or granulating processes. They further may be used in the form of an extract, a tablet or powdered medicine by mixing with a variety of mas or bonding agents. Furthermore, they can be used in the form of drinkable, syrup or emulsion.

We ascertained that it is clinically effective to administrate the eggs containing a high amount of iodine so that the total iodine content may be 500 to 2000 μg per day. Therefore, where hen's eggs of which the iodine content is about 500 μg to 1000 μg per egg are used, the composite of the invention can be ingested very easily and continuously in a daily life, because the number of eggs to be eaten is only one or two per day. And, the composite is preferably administrated for over three consecutive weeks, because it does not have an immediate effect but an slow effect.

The result of an acute virulence test of the composite is summarized as follows:

| Acute Virulence Test | | | |
|---|---|---|---|
| Animals used: | Rats, Wister descent | Sex: | Female |
| Weight: | 100 to 110g | Number: | 10 heads |

In this test, powdered egg containing much iodine was used, and it was orally dosed to the rats at a dosage increased in geometric ratio to the maximum of 50 mg of iodine amount per kg of the rat's weight, and then the rats were observed after seven days. In the result, none of the rats died nor even lost their weight. Thus, the composite of the present invention was proved not to have any acute virulence.

Then, we made clinical experiments of the composite on the effect for treating diabetes. The result of them are as follows:

Clinical Experiment 1

Eggs of the example 1 mentioned later which contain iodine of 500 to 600 μg per egg were dosed to a male diabetic patient of forty-eight years old at the rate of three eggs per day for twenty-four days. The patient was put on a restricted diet through the above period, and synthetic medicines for diabetes were not dosed at all.

Blood sugar value, urine sugar value and insulin amount were determined both before dosing and after dosing. The composite of the invention was proved to have a very remarkable effect as shown in Table 1.

TABLE 1

| | Blood sugar mg/dl | Urine sugar g/dl | Insulin μU/ml |
|---|---|---|---|
| Before dosing | | | |
| Before a Meal | 309 | 1.5 | 11 |
| 30 minutes after a meal | 371 | 2.0 | 15 |
| 60 minutes after a meal | 456 | 6.0 | 11 |
| 120 minutes after a meal | 425 | 8.0 | 10 |
| 180 minutes after a meal | 440 | 6.0 | 11 |
| 21 days after dosing | | | |
| Before a meal | 104 | 0 | 19 |
| 30 minutes after a meal | 97 | 0 | 24 |
| 60 minutes after a meal | 163 | 0 | 53 |
| 120 minutes after a meal | 109 | 0 | 33 |

TABLE 1-continued

|  | Blood sugar mg/dl | Urine sugar g/dl | Insulin μU/ml |
|---|---|---|---|
| 180 minutes after a meal | 73 | 0 | 18 |

*the above values were obtained by means of grape sugar loading test.

Clinical Experiment 2

The above eggs of the example 1 were dosed to a male diabetic patient of fifty-five years old for three months at the rate of two eggs per day. Also, in this experiment, the patient was put on a restricted diet, and other synthetic medicines for diabetes treatment were not dosed.

Blood sugar value, urine sugar value and insulin amount were determined before dosing, during dosing and after dosing. The determination results are shown in Table 2.

TABLE 2

|  | Blood sugar mg/dl | Urine sugar g/dl | Insulin μU/ml |
|---|---|---|---|
| Before dosing |  |  |  |
| Before a meal | 246 | 4.0 | not determined |
| 30 minutes after a meal | 355 | impossible to get urine | " |
| 60 minutes after a meal | 560 | 6.0 | " |
| 120 minutes after a meal | 522 | 8.0 | " |
| 180 minutes after a meal | 446 | 8.0 | " |
| 12 days after dosing |  |  |  |
| Before a meal | 193 | impossible to get urine | 6 |
| 30 minutes after a meal | 339 | impossible to get urine | 6 |
| 60 minutes after a meal | 501 | impossible to get urine | 9 |
| 120 minutes after a meal | 402 | 6.0 | 10 |
| 180 minutes after a meal | 330 | impossible to get urine | 8 |
| 3 months after dosing |  |  |  |
| Before a meal | 61 | 0 | 17 |
| 30 minutes after a meal | 135 | 0 | 16 |
| 60 minutes after a meal | 176 | 0 | 28 |
| 120 minutes after a meal | 136 | 0 | 24 |
| 180 minutes after a meal | 123 | 0 | 21 |
| 30 minutes after a lunch | 150 | 0 | 18 |
| 60 minutes after a lunch | 131 | 0 | 10 |

*The above values were obtained by means of grape sugar loading test

Clinical Experiment 3

The said eggs of the example 1 were dosed to a male diabetic patient of forty-five years old for eighty-five days at the rate of two eggs per day. Also, in the case of the experiment, the patient was put on the restricted diet, and any synthetic medicines for diabetes treatment were not dosed. Blood sugar value, urine sugar value and insulin amount were determined before dosing, during dosing and after dosing. The results are shown in Table 3.

TABLE 3

|  | Blood sugar mg/dl | Urine sugar g/dl | Insulin μU/ml |
|---|---|---|---|
| Before dosing |  |  |  |
| Before a meal |  |  |  |
| 30 minutes after a meal | 251 | 8.0 | not determined |
| 60 minutes after a meal | 309 | 2.0 | " |
| 120 minutes after a meal | 331 | 4.0 | " |
| 180 minutes after a meal | 317 | 4.0 | " |
| 25 days after dosing |  |  |  |
| Before a meal | 216 | 1.5 | 9 |
| 30 minutes after a meal | 182 | 0.1 | 0 |
| 60 minutes after a meal | 213 | 0.5 | 0 |
| 120 minutes after a meal | 237 | 1.5 | 0 |
| 180 minutes after a meal | 262 | 1.5 | 5 |
| 85 days after dosing |  |  |  |
| Before a meal | 88 | 0 | 10 |
| 30 minutes after a meal | 171 | 0 | 25 |
| 60 minutes after a meal | 176 | 0.1 | 30 |
| 120 minutes after a meal | 92 | 0 | 18 |
| 180 minutes after a meal | 74 | 0 | 13 |

*The above values were obtained by means of grape sugar loading test

There are many clinical experiments similar to the above experiments, and they prove that the composite of the present invention is effective in treating diabetes.

Although the causality of the treatment effect of diabetes are never apparent, it is supposed that the composite of the invention ingested by diabetic patients will gradually normalize internal metabolism and the function of an endocrine gland, and thereby promote insulin secretion.

The composite of the invention does not have any adverse effect or reaction, and is effective not only in diabetes itself but also in secondary diseases thereof. The composite of the invention may be called as an ideal composite for diabetes treatment, because it is made of or from eggs containing a high amount of iodine, and it can be used or ingested as a part of dietary cure.

EXAMPLE 1

Calcium iodate was added to a feed for hens on the market so that the iodine content became 100 ppm, and the feed was fed to hens of fifty heads which had begun to lay eggs three months ago. Thus ten days after the feeding, eggs containing iodine of 550 μg per egg on an average were produced. Remarkable recovery effect was ascertained in eight of eleven patients to whom the above eggs were dosed.

EXAMPLE 2

Calcium iodate was added to a hen's feed on the market so that the iodine contact became 1,000 ppm, and powdered seaweed was further added to the admixture by 1 percent. The feed was fed to hens of 100 heads that had begun to lay eggs five months ago.

The eggs of 160 kg obtained by the said feeding were dried by a spray-dryer, and thereby the present composite of 32 kg was produced. The composite in the form of powdered egg contained iodine of 212 mg/kg.

EXAMPLE 3

Sodium iodate was added to a hen's feed on the market so that the iodine content became 150 ppm, and then there were obtained eggs containing iodine of 1.300 μg per egg on an average by the same method as the Example 1. The eggs were then broken, and dextrin was added to them by 10 percent. After adding water to the admixture, they were sufficiently mixed, and then spray-dried by a spray-drying apparatus, whereby the composite of the invention was obtained.

EXAMPLE 4

Sodium iodate was added to a hen's feed on the market so that the iodine contact became 75 ppm, and there were obtained eggs containing iodine of 480 μg on an average by the same method as Example 1. The composite of the present invention was produced by freeze-drying the above eggs.

We claim:

1. A method of treating diabetic patients which comprises dosing said patient with one or more eggs containing from 300 μg to 2,000 μg of iodine so that the total dosage is from 300 μg to 2,000 μg of iodine.

* * * * *